Figure 1:
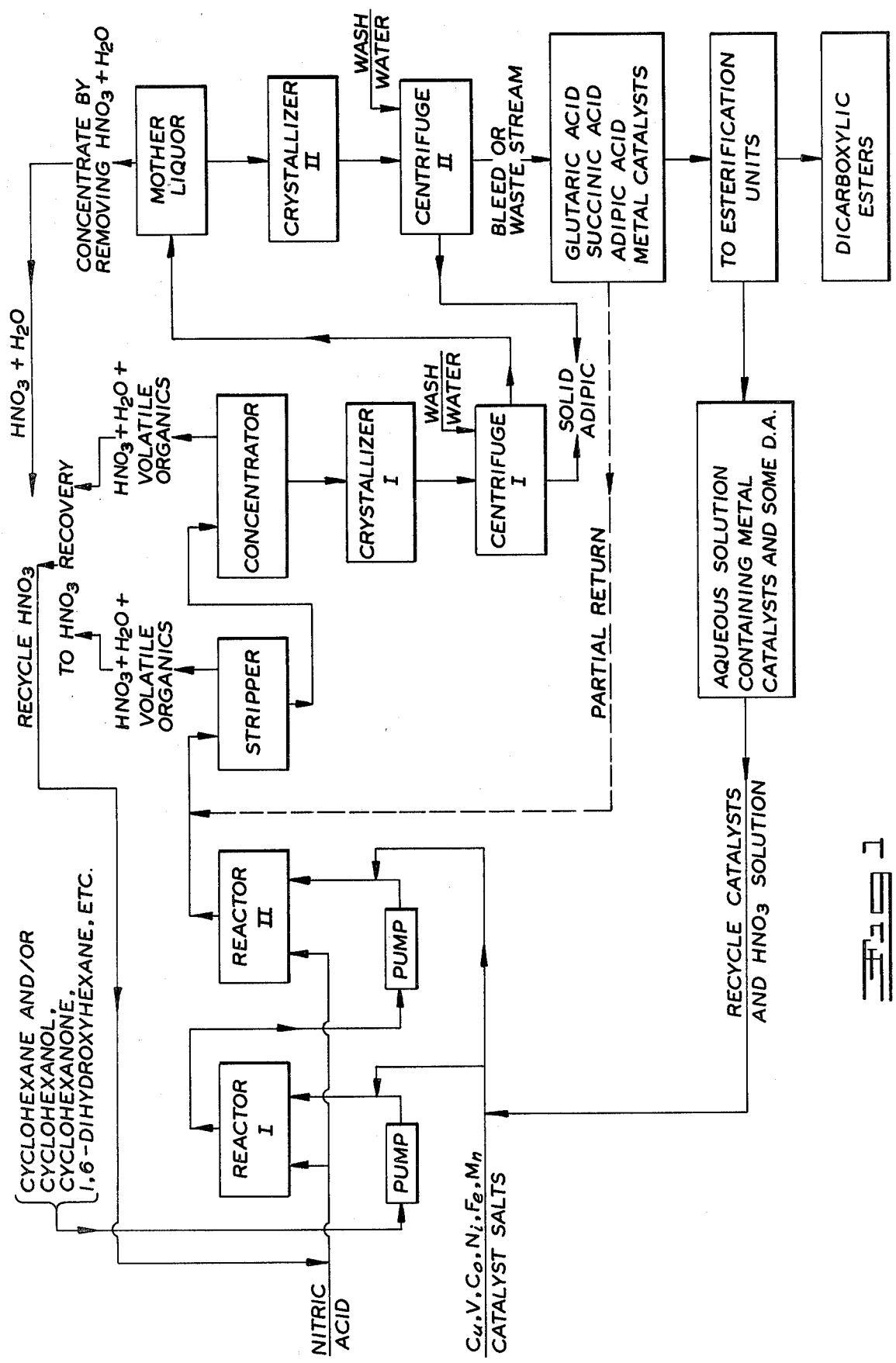

United States Patent [19]

Kuceski

[11] 4,375,552

[45] Mar. 1, 1983

[54] NITRIC ACID PROCESS FOR PRODUCTION OF ADIPIC ACID FROM HYDROCARBONS

[75] Inventor: Vincent P. Kuceski, Chicago Heights, Ill.

[73] Assignee: C. P. Hall Company

[21] Appl. No.: 46,030

[22] Filed: Jun. 15, 1970

Related U.S. Application Data

[63] Continuation-in-part of Ser. No. 795,419, Jan. 31, 1969, abandoned.

[51] Int. Cl.$^3$ .............................................. C07C 67/08
[52] U.S. Cl. ................................... 560/204; 560/191; 560/193; 560/198; 562/528; 562/529; 562/530; 562/540; 562/549; 562/590; 562/593
[58] Field of Search ............... 260/485, 485 S, 533 C, 260/531, 537 O; 560/191, 204, 193, 198; 562/528, 529, 530, 540, 543, 549

[56] References Cited

U.S. PATENT DOCUMENTS

| | | | |
|---|---|---|---|
| 2,824,122 | 2/1958 | Kuceski | 260/537 |
| 2,968,674 | 1/1961 | Franke et al. | 260/485 |
| 3,329,712 | 7/1967 | Danly et al. | 260/537 |

FOREIGN PATENT DOCUMENTS

| | | |
|---|---|---|
| 705578 | 3/1941 | Fed. Rep. of Germany ...... 260/537 |
| 305308 | 2/1929 | United Kingdom . |
| 494611 | 10/1938 | United Kingdom . |
| 933714 | 8/1963 | United Kingdom . |

*Primary Examiner*—Natalie Trousof
*Assistant Examiner*—Vera C. Clarke
*Attorney, Agent, or Firm*—Frease & Bishop

[57] ABSTRACT

Waste streams from adipic acid manufacture containing nitric, succinic, glutaric and adipic acids and valuable catalytic metal as salts are treated with alcohols, thereby separating, as esters, succinic and glutaric acids which would contaminate pure adipic acid on recycling, and allowing the re-use of the resulting stream containing nitric acid and metal catalytic salts.

9 Claims, 2 Drawing Figures

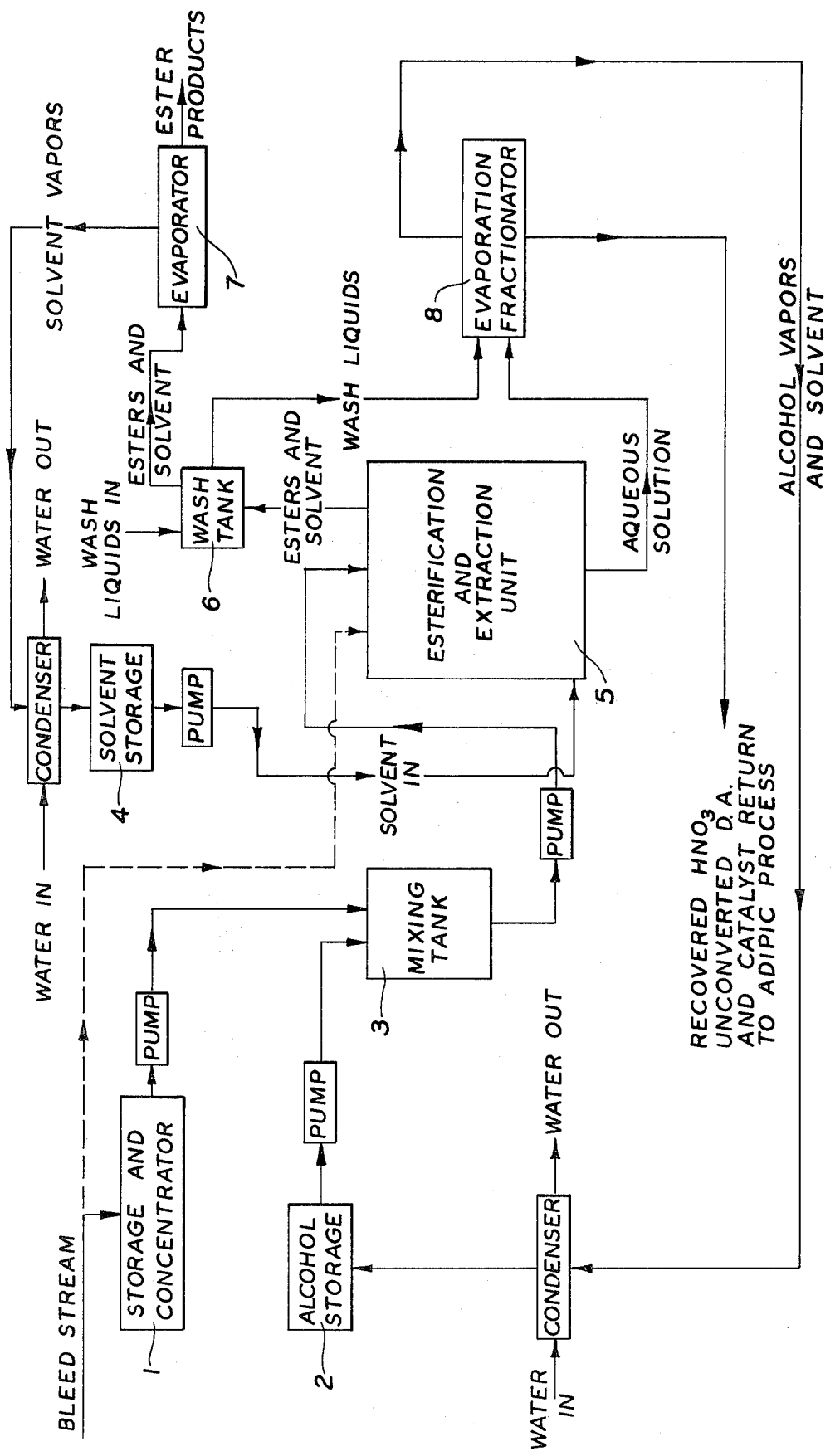

NITRIC ACID PROCESS FOR PRODUCTION OF ADIPIC ACID FROM HYDROCARBONS

This application is a continuation-in-part of my application Ser. No. 795,419 filed Jan. 31, 1969, now abandoned.

This invention relates to the recovery of economic values from aqueous waste streams resulting from the nitric acid oxidation of organic source material, using metal nitrate catalyst. The source material is usually a material from the class consisting of saturated and unsaturated cyclic and acyclic hydrocarbons and oxygen-containing derivatives thereof, which hydrocarbons and derivatives contain at least 6 carbon atoms in a straight or cyclic saturated chain. The invention includes the recovery of the dicarboxylic acids as esters and the separation of catalyst, other metal salts and nitrogen-containing organic material as an aqueous solution. The dicarboxylic acids are separated from the solution as esters, and the solution containing the catalyst is reused in the process.

This invention more particularly relates to the waste or bleed stream from a nitric-acid oxidation plant in which adipic acid is produced for the manufacture of nylon.

The waste stream from such an adipic-acid plant contains valuable dicarboxylic acids in addition to adipic acid, catalysts and nitric acids. Such streams are called "waste streams" because they become contaminated with impurities, and heretofore it has been necessry to dispose of them after some reuse together with the valuable dicarboxylic acids and catalytic salts which they contain. Such waste streams are also called "bleed streams."

It is well known that the process of obtaining adipic acid from such aqueous solutions of sufficient purity for nylon manufacture, requires that the acid be crystallized, free of unwanted metal salts and nitrogen-containing compounds, and substantially free of other organic acids than adipic acid.

An article describing the process of producing adipic acid using cyclohexane as source material together with a diagrammatic flow sheet is described on pages 74–79 of the May 1956 issue of Petroleum Processing. A similar diagram is included herein. The article contains many references; and the art on production of adipic acid is well covered in the literature.

According to this invention, adipic acid is crystallized and recovered in a very pure state, substantially entirely free of contaminants, and succinic, adipic and glutaric acid esters are separated, all without separating the catalyst from the aqueous solution containing the acid, and the aqueous solution is reused. The process is described in connection with the accompanying flow sheets, in which FIG. 1 is a flow sheet of the adipic acid process and FIG. 2 is a more detailed flow sheet of the esterification process.

As indicated in FIG. 1, the hydrocarbon usually employed in the production of adipic acid is a cyclic hydrocarbon and, more generally, cyclohexane is used. Other hydrocarbons which may be used include cyclohexanol, cyclohexanone, 1,6-dihydroxyhexane, etc. The hydrocarbon and nitric acid are reacted in the presence of a catalyst in a reactor. The catalyst is usually added as a metal powder or a salt. It is usually copper, which often is mixed with vanadium, but it is not necessary that it be used alone, because one or more other metals may be used, including manganese, nickel, iron, chromium, molybdenum, mercury and barium, etc.

From the reactor the reaction mixture goes to a stripper where nitric acid and water and volatile organics are vaporized. The vapors go to a nitric-acid recovery system and the nitric acid obtained is recycled. From the stripper the solution goes to a concentrator where more nitric acid and water and volatile organics are vaporized and combined with the like vapor from the stripper. The concentrated solution goes to a crystallizing system and from each crystallizer to a centrifuge or the like. Usually a series of crystallizer-centrifuge units will be used although only two are shown in the drawing. Between each two such crystallizing units there is usually a concentrator for concentrating the mother liquor obtained. The solid adipic acid which is recovered is of high purity.

The bleed or waste stream from the crystallizing system includes various materials such as small amounts of glutaric, succinic and adipic acids and $HNO_3$, in addition to catalyst and other impurities such as other nitrogen-containing compounds, other metal salts derived from the equipment, etc. A certain amount of the waste stream may be returned into the system at any advantageous point between the reactor and the first crystallizer unit. The remaining waste stream (or all of the waste stream, if none is returned) goes to an esterification system where dicarboxylic acids are separated without affecting the catalyst which is in this solution, and is returned to the system for re-use. An esterification system is diagrammed in FIG. 2.

In the esterification system the acids will be treated with an alcohol such as methyl, ethyl, propyl, butyl, hexyl, octyl, decyl, or other hydroxy-containing compounds, including polyols such as ethylene glycol, diethylene glycol, butane diol, propylene glycol or other alcohol, etc. Unsaturated or cyclic alcohols which may have primary or secondary hydroxyl groups, but usually not tertiary hydroxyl groups, may be used. The alcohol may contain other groups such as carbonyl groups, nitro groups, halogens, ester and ether groups, etc. If the alcohol used produces ester which does not separate easily from the aqueous phase, an immiscible solvent may be used to extract the ester.

Organic solvents with a boiling range of about 0° C. to 200° C. may be used, using superatmospheric pressure when desired. A solvent such as cyclohexane, cyclohexanol, cyclohexanone or combinations of these is used to advantage since they are source materials used in the manufacture of adipic acid and are conveniently available and may be easily recovered for recycling to the oxidation reactor when they become contaminated. Other solvents which may be used include alkanes (straight or branched chain) containing 3 to 8 or 10 carbon atoms, including hexane, pentane, butane, propane, toluene, benzene, etc. Petroleum solvents may be used such as naphthenes and naphthas, including V,M and P (varnish makers and painters) naphtha, etc. Aromatic solvents which can be used very satisfactorily include benzene, toluene, xylene, ethyl benzene, etc. Halogenated aliphatic hydrocarbon solvents which may be used include carbon tetrachloride, methylene chloride, ethylene dichloride, 1,1,1-trichloroethane, trichloroethylene, chloroform, and the corresponding bromine compounds and mixed halogenated aliphatic hydrocarbons including, for example, $CCl_3F$, $CCl_2F.CClF_2$, $CCl_2FCCl_2F$, etc. The halogenated aromatic solvents which can be used include chlorobenzene, bromobenzene, chlorotoluene, etc. Ethers which may be used include dichlorodiisopropyl ether and di-n-butyl ether, methyl phenyl ether, ethyl butyl ether, etc. Ketones other than cyclohexanone which may be used include dipropyl ketone, dibutyl ketone, ethyl butyl ketone, etc. If a solvent stable to nitric acid oxidation is desired, benzene may be used, or even some of the fluorinated hydrocarbons.

The bleed or waste stream from an adipic-acid plant may contain either high or low concentrations of the soluble dicarboxylic acids and metal catalyst salts. It is preferred that the bleed stream be concentrated as much as possible to facilitate the desired esterification step; however, the esterification reaction proceeds to some extent even at very low concentrations. The object is to remove as much as possible of the dicarboxylic acids by esterification in order to recycle a stream containing as little as possible of adipic acid and contaminating succinic and glutaric acid. U.S. Pat. No. 2,824,122 describes in detail a mechanism of esterification of dicarboxylic acids from aqueous solutions which may be used, but does not refer to cyclic procedure or the details of a cyclic operation which result in the advantages disclosed herein. The nitric acid in the bleed stream provides sufficient catalytic activity for the esterification reaction. If, by chance, all of the nitric acid were removed, nitric acid may be added to provide catalysis of the esterification reaction. Only a small amount is needed; from as little as 0.01 percent to 2 percent based on the weight of the stream is usually sufficient. Other acid catalysts can also be used such as sulfuric, phosphoric, hydrochloric, etc.

The esterification reaction produces esters and these esters are either insoluble in the aqueous reaction mixture or are made insoluble in it by adding an immiscible solvent. The reaction mixture thus become a two-phase system and the phases are separated, for instance by gravity or centrifuging. The nonaqueous layer is usually the lighter liquid, and this may be accumulated in a vessel for later use or returned continuously to the cycle, and the solvent and excess alkanol are stripped from the solution. However, in most cases the esterification is not complete and further esterification is required to complete the esterification of any carboxyl groups. To complete the esterification, excess alkanol may be added together with HNO$_3$ catalyst if required, and the esterification reaction continued until all or nearly all free carboxylic acid groups are esterified. The solvent may or may not be present at this stage, and often the solvent will not be stripped in order to aid in the steps of neutralizing and washing the esters.

The heavier layer is usually the aqueous layer which contains some remaining unesterified dicarboxylic acids, some partially esterified acids, nitro-compounds, catalysts, and metalsalt contaminates. (The metal salts which contaminate the solution are those salts which come from the equipment. These salts can be the chromium, nickel and iron from stainless steel equipment, or silicon salts from glass equipment, or vanadium and tantalum salts from more sophisticated equipment.) The aqueous layer also contains some of the alkanol and may contain entrained solvent when a solvent is used. This aqueous layer is stripped of the alkanol and the solvent, if any, by heat or vacuum, or both, and the recovered alkanol and solvent is then recycled to the esterification unit or oxidizing unit as required. Such aqueous layer can then be recycled to the oxidizers and the catalysts dissolved therein can be used directly without further processing as catalysts for the oxidation of hydrocarbon source materials to adipic acid. Any metal salts which do not have catalytic value derived from the equipment are present in negligible quantity and do not affect the course of the oxidation reaction.

Higher boiling alcohols, including polyols, may be used in the esterification to produce valuable plasticizers.

The following examples are illustrative. They are advantageously carried out on a continuous basis, with continuous return of the aqueous solution which is produced, to the cycle. Alternatively, they may be carried out on a batch basis with continuous return of the aqueous solution to the cycle.

If methanol is used as the alcohol, the reaction products in the esterification-extractor are separated on extraction with a water-immiscible solvent in the manner indicated in the following diagram:

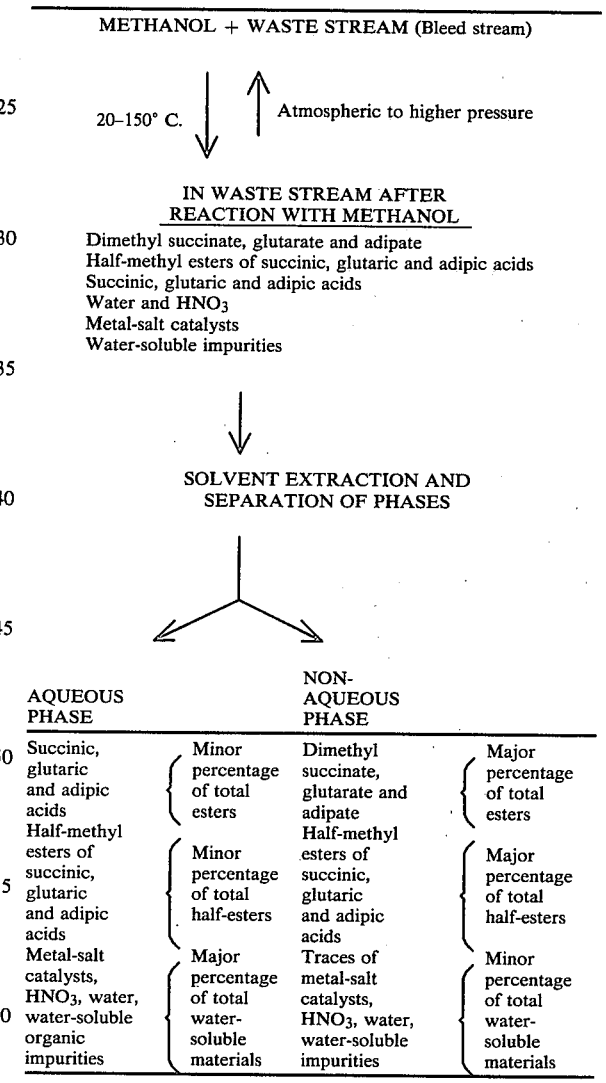

In FIG 2 we show a schematic diagram of the continuous process of this invention.

Tank 1 of FIG. 2 is a storage tank for the bleedstream or wastestream obtained from the adipic acid manufacturing plant shown in FIG. 1. The bleedstream may be used as is or may be concentrated to higher percentage solids of dicarboxylic acids. This solution may be pumped to a mixing tank 3 to which alcohol is added from storage tank 2 for alcohol. Alternatively, the bleedstream may be fed directly to the top of the esterification and extractor unit 5 and the alcohol from storage tank 2 may be fed simultaneously to this unit 5. The amount of alcohol to be added with the bleedstream will be determined by the amount of dicarboxylic acids and monocarboxylic acids present in the bleedstream and also by the extent of extraction desired. In the esterification and extractor unit 5, there is a settling area at the top and another at the bottom. The alcohol bleedstream solution is fed at the top while the selected solvent is fed at the bottom so that the two solutions pass each other countercurrently. The solvent must have a sufficiently different specific gravity from the aqueous phase to permit separation of the phases. It may be lighter or heavier than the aqueous phase. If the solvent is lighter, it passes in contact first with the most depleted aqueous solution of esters and finally passes through the top of the extractor through the most concentrated aqueous solution of esters. As the aqueous solution of the esters passes down, it is progressively weakened with respect to dicarboxylic acid content and ester content. The aqueous solution is then passed to an evaporator 8 where residual alcohol and solvent are removed. The alcohol thus removed is both unreacted alcohol and alcohol split off by hydrolysis during evaporation. This solution from the evaporator containing mostly alcohol and some solvent and water can be returned directly to alcohol storage tank 2 or fed into the top of the esterification and extractor unit 5.

The solvent solution containing esters, half-esters and some dicarboxylic acid is pumped or overflowed from the esterification and extraction unit 5 to wash tank 6 which is used to water-wash the esters free of water-soluble dicarboxylic acids, nitric acid, and catalyst. Alternatively, this wash solution may be returned to the evaporator 8. The aqueous solution, stripped continuously in evaporator 8, now contains nitric acid, some residual dicarboxylic acids, catalyst and water. This is pumped back to the original adipic process; it may be concentrated before return to the process.

Evaporator 7 receives the washed solvent and ester phase from tank 6 where the solvent is removed and returned to solvent storage. Some methanol is also removed and returned to the process. Water is also removed or the esters remaining after removal of solvent in evaporator 7 may be used as such as they may be reacted with a further quantity of alcohol to complete esterification if desired.

If desired, the esters may be hydrolyzed with water to recover the dicarboxylic acids themselves or they may be pumped to a fractionating column where the pure esters may be distilled and purified as described in U.S. Pat. No. 2,824,123. The esters, if they contain nitro compounds, may also be purified by washing with alkaline solutions in wash tank 6 according to the teachings of U.S. Pat. No. 3,021,348.

EXAMPLE 1

In a continuous esterification extractor (see FIG. 2), we introduce continuously, at the top, 100 parts by weight of an aqueous solution having the following analysis:

| | % D.A.* | | D.A. (100% Basis) |
|---|---|---|---|
| Succinic acid | 5.77 | | 25% |
| Glutaric acid | 13.58 | 23.04 | 59% |
| Adipic acid | 3.69 | | 16% |
| Other organic compounds including M.A.** | 2.00 | | 100% |
| HNO₃ | 8.45 | | |
| Water and catalyst | 66.51 | | |
| Total | 100.00 | | |

*Dicarboxylic Acids.
**Monocarboxylic Acids.

At the same time, we introduce into the aqueous phase, either before it enters the column 5, during, or after it enters the column, a stream of methanol at the rate of from 10 to 100 parts by volume of methanol.

The flow of aqueous solution is regulated so that an average contact time of 30 minutes is provided in the extractor.

The following reactions are taking place in the column:

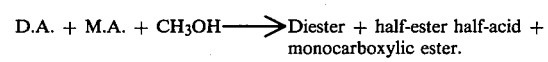

D.A. + M.A. + CH$_3$OH ⟶ Diester + half-ester half-acid + monocarboxylic ester.

As an extracting solvent, into the lower end of the column, 100 parts by volume of cyclohexane at 60° C. is passed through in 10 minutes with the results recorded in the first double column of the following table.

| METHANOL | D.A. ESTERS EXTRACTED AT A COUNTERCURRENT FLOW OF: | | | |
|---|---|---|---|---|
| Parts per 100 of | 100 parts cyclohexane | | 1000 parts cyclohexane | |
| aqueous phase | Parts | % | Parts | % |
| 10 | 0.2 | 0.9 | 1.5 | 6.5 |
| 20 | 0.3 | 1.3 | 2.5 | 10.8 |
| 30 | 0.5 | 2.2 | 4.0 | 17.3 |
| 40 | 1.0 | 4.3 | 7.0 | 30.2 |
| 50 | 1.3 | 5.7 | 10.0 | 43.4 |
| 100 | 2.0 | 8.7 | 14.0 | 60.8 |

The extraction of the above aqueous-methanol solution of 1000 parts of cyclohexane as recorded in the second double column of the above table was done on a more dilute solution (12%) than the original solution containing 23.04% D.A.

The solvent continuously extracts the diesters, half-esters, and monocarboxylic acid esters. The solvent-mixture is then continuously washed with water to remove water-soluble substances and then the solvent is stripped leaving the ester products to be processed as desired. If the esters are not completely esterified, they may be finished by adding more alcohol and reacting to reduce acid value. Or they may be distilled directly to fractionate the different esters, half-esters, and mono-esters from each other.

EXAMPLE 2

This example illustrates the use of a water-insoluble alcohol which forms water-insoluble esters which normally do not require the addition of an immiscible solvent in order to form a non-aqueous phase.

An aqueous solution of dicarboxylic acids and metal catalyst salts from the bleed stream of an adipic-acid plant of the following composition is used:

|  | PARTS BY WEIGHT |
| --- | --- |
| HNO$_3$ | 7 |
| Succinic acid | 5 |
| Glutaric acid | 21 |
| Adipic acid | 6 |
| Cu—V catalyst salts | 2.2 |
| Water | 58.3 |

This solution is further concentrated by removal of water to give a solution with the following composition:

|  | PARTS BY WEIGHT |
| --- | --- |
| HNO$_3$ | 7 |
| Succinic acid | 5 |
| Glutaric acid | 21 |
| Adipic acid | 6 |
| Cu—V catalyst salts | 2.2 |
| Water | 39.0 |
|  | 80.2 |

The concentrated solution is then reacted with 90 parts of isononyl alcohol by heating to the boiling point at atmospheric pressure, thus removing more water from the concentrated solution. The water removed is both water of solution and water of esterification. The reaction proceeds at a rate equal to the speed of removal of water. Thus, the water is removed during the reaction cycle. Twenty-five parts of water is removed and isononyl alcohol removed by vaporization is replaced.

The system is a two-phase system throughout the reaction period and a solvent is not necessary to separate the phase, although a solvent may be used to facilitate separation of the phases.

Upon separation of the two phases without solvent we obtain the following composition in each phase in parts backcalculated to the original materials as acids and isononyl alcohol. All compounds are given in parts by weight.

|  | AQUEOUS PHASE | NON-AQUEOUS PHASE |  |
| --- | --- | --- | --- |
| HNO$_3$ | 6.0 | 0.5 |  |
| Succinic acid | 2.0 | 3.0 | in mono- and |
| Glutaric acid | 4.0 | 17.0 | di- isononyl |
| Adipic acid | 1.0 | 5.0 | alcohol esters |
| Isononyl alcohol | 1.0 | 89.0 | in esters of dicarboxylic acid and as free alcohol |
| Metal-salt catalysts | 2.2 | Traces |  |
| Water | 20.0 | 2.0 |  |
|  | 37.2 | 116.5 |  |

The aqueous phase is recycled to use its catalyst content.

The two columns of figures add up to more than the input because the acids tied up as esters are listed according to their weights as acids when actually water of esterification was removed to the non-aqueous phase.

The non-aqueous phase is then washed with water to remove remaining traces of nitric acid and metal-salt catalysts. The non-aqueous phase now contains:
50 parts di-isononyl esters of succinic, glutaric, and adipic acids
35 parts half-esters of succinic, glutaric, and adipic acids
29 parts of free isononyl alcohol.

This reaction mixture is transferred to a glass vessel and the reaction is continued by addition of 0.2 percent sulfuric acid. The esterification of half-esters is completed in 3 hours and then the esters are washed with alkali solutions as described in U.S. Pat. Nos. 2,824,122 and 3,021,348 to remove remaining acidic components and nitrogen-containing compounds.

The esterification mixture is then stripped of free isononyl alcohol and bleached with sodium hypochlorite and hydrogen peroxide to give a light-colored di-ester suitable as plasticizer for polymers such as PVC. The di-ester may be distilled to further purify it.

The aqueous phase is now steam stripped to remove any remaining alcohol and then returned to the oxidizers in the reaction cycle. The metal catalyst salts contained therein are still reactive and fully effective in the promotion of the oxidation reaction.

EXAMPLE 3

This example illustrates the use of an aromatic base alcohol in the process of this invention.

A bleed stream having the composition given in Example 2 is used. However, the solution is not concentrated but used directly in a reaction with benzyl alcohol. To 100 parts of the original solution is added 100 parts of benzyl alcohol and the reaction mixture is boiled. It is understood, of course, that the addition of benzyl alcohol can be made to a bleed stream in a continuous manner with continuous esterification and separation of phases and continuous recycle of aqueous solutions back to the reactors.

During the reaction, 40 parts of water and 20 parts of benzyl alcohol are removed by vaporization. The water removed is both water of solution and water of esterification. The amount of benzyl alcohol consumed is minimized by recycling vaporized benzyl alcohol back to the reactors.

The reaction mixture is then separated into aqueous and non-aqueous phases and the following balance of materials obtained:

|  | PARTS OF AQUEOUS PHASE | PARTS OF NON-AQUEOUS PHASE |  |
| --- | --- | --- | --- |
| HNO$_3$ | 6 | 0.5 |  |
| Succinic acid | 1 |  | Total of mono- and di- esters of benzyl alcohol and succinic, glutaric, adipic and free benzyl alcohol |
| Glutaric acid | 3 | 97.0 |  |
| Adipic acid | 1 |  |  |
| Half-esters and benzyl alcohol | 1 |  |  |
| Metal salt catalysts | 2.2 | Traces |  |
| Water | 25.5 | 2.5 |  |
|  | 39.7 | 100.0 |  |

The aqueous phase is steam-stripped to remove free benzyl alcohol and also to hydrolyze and remove any esterified benzyl alcohol. The remaining aqueous phase with the following analysis is returned to the system, more than 80 percent of the dicarboxylic acids having been removed without removing any appreciable amount of valuable catalyst metal salt or nitric acid.

|  | PERCENT |
| --- | --- |
| HNO₃ | 15 |
| Succinic acid | 2.5 |
| Glutaric acid | 9.0 |
| Adipic acid | 2.5 |
| Cu—V salts of metal catalyst | 4.7 |
| Water | 66.3 |

The upper phase or esterified alcohol layer is reacted further with the excess benzyl alcohol in the mixture, washed with water, neutralized, and distilled to yield a mixture of plasticizer esters of the following composition:

| Light ends | 0.5 |
| --- | --- |
| Dibenzyl succinate | 15.0 |
| Dibenzyl glutarate | 68.0 |
| Dibenzyl adipate | 15.0 |
| Heavy ends | 1.5 |

The aqueous phase which retains the catalyst and is substantially free of dicarboxylic acids and esters, is returned to the oxidation cycle.

EXAMPLE 4

This example illustrates the use of a polyol in the practice of this invention.

Using the waste stream of Example 2 we bring about a series of reactions between a waste stream containing dicarboxylic acids of the formulae HOOC-$X_n$—COOH in which $n=2$, 3 and 4 and X is an alkylene radical such as:

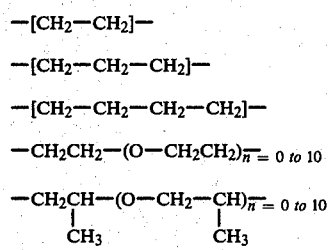

in which there are two hydroxy groups of which the following equations are illustrative:

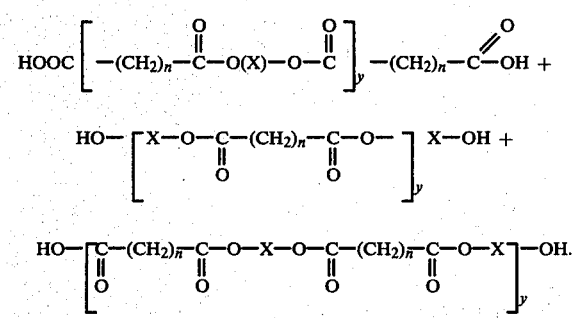

In the equation, y is an integer of 1 to 10 or more.

If polyols of more than two hydroxyls are used more complex polyesters will result.

Generally, the polyesters will be extracted with a non-aqueous solvent and the esterification finished off as illustrated previously in Examples 1–3.

More specifically we illustrate with the use of butanediol:

100 parts of the waste stream from Example 1 is reacted with 31 parts of butanediol and during the reaction 40 parts of water is removed. The one-phase aqueous mixture is more viscous as water is removed. Urea is added as required if oxidation takes place as evidenced by evolution of nitrogen oxides. The urea is used to stop or inhibit this reaction.

The remaining solution is extracted in a continuous extractor with benzene to remove the polyester from the aqueous phase. The benzene also extracts the excess of unreacted butanediol from the aqueous phase.

The aqueous phase is then separated and is found to have the following composition:

|  | PARTS BY WEIGHT |
| --- | --- |
| HNO₃ | 6.5 |
| Succinic, glutaric, and adipic butanediol esters | 2.0 |
| Succinic acid | 1.0 |
| Glutaric acid | 2.0 |
| Adipic acid | 1.0 |
| Butanediol | 5.0 |
| Metal catalyst salts | 2.2 |
| Water | 20.0 |
| Benzene | 0.5. |

The aqueous solution is then steam distilled to remove all the benzene and about 4 parts of the butanediol and the solution can then be returned to the oxidizer system for re-use of the catalysts and nitric acid. Remaining butanediol does not affect the reaction in the oxidizer and does not present any contamination problem because it is catalyzed to succinic acid in the oxidizers.

The non-aqueous phase, containing benzene is found to contain both carboxy- and hydroxy-terminated compounds and the quantity is estimated to be 45 parts. It also contains acidity equivalent to an acid value of 50 mgs. of KOH per gram. The benzene layer is washed once with 10 parts of water to remove any free butanediol and then the reaction mixture is heated to complete esterification, to lengthen the polyester chain, and to remove water and benzene. A small amount (0.17) of sulfuric acid and catalyst is added to take the place of some of the nitric acid lost during the small water-wash. After this step the acid value is reduced to 30 mgs. of KOH per gram and at this point alkanol is added, hexanol in this case, 5 parts, and the mixture boiled to reduce acid value and benzene content. When the acid value becomes 10 or less the reaction mixture is washed with water and neutralized, again stripped of benzene and dried. The yield of polyester was 47 parts having a molecular weight of between 200 and 1500. The polyester is useful as a plasticizer in polymers.

The aqueous solution which contains metal-salt catalyst is reused in the oxidation to produce additional adipic, glutaric and succinic acids.

EXAMPLE 5

Cyclohexanol is an ideal alcohol for use in the process of this invention since it is produced from oxidation of cyclohexane in the production of adipic, glutaric and succinic acids and is available on the site of the adipic-acid plant.

Using the same proportions and process of Example 3 an aqueous layer is produced which does not need stripping before return of the solution for re-use of the catalytic metal salts because cyclohexanol is a raw material for the oxidation to adipic acid.

The lower aqueous phase has the following composition after separation:

|  |  |
|---|---|
| HNO3 | 14 |
| Succinic acid | 3.0 |
| Glutaric acid | 5 |
| Adipic acid | 3.5 |
| Cu—V catalyst salts | 4.5 |
| Water | 70.0 |

The upper phase yields a diester with the following composition:

|  |  |
|---|---|
| di-cyclohexanol succinate | 14 |
| di-cyclohexanol glutarate | 70 |
| di-cyclohexanol adipate | 15. |

EXAMPLE 6

In this example we show the use of toluene in simple extractions of the dimethyl esters from the dicarboxylic acid solutions. The procedure was as follows:

One hundred ml. (114 grams) of a 30 percent solids solution having the following analysis:

|  | % |
|---|---|
| Succinic acid | 7.0 |
| Glutaric acid | 16.0 |
| Adipic acid | 5.0 |
| Other organic compounds | 1.5 |
| HNO3 | 6.0 |
| Water and catalyst | 64.5 |
|  | 100.0 | was reacted with 50 ml. methanol and 60 ml. toluene. About 28 percent of the solution or about 32 grams consisted of D.A. Results are shown below.

| BOILING TIME | GRAMS ESTER FORMED | % OF SOLIDS | CUM. % |
|---|---|---|---|
| Up to boiling Temp. | 16.1 | 50.2 | 50.2 |
| After 5 min. boiling | 9.05 | 23.2 | 73.4 |
| After additional 10 min. boiling | 4.6 | 14.3 | 87.7 |
| TOTAL | 29.75 | 87.7 |  |

Before each boiling period, 60 ml. of toluene was added. The solution was cooled to 40° C. and the toluene phase separated. The toluene was evaporated to remove toluene solvent and the extracted esters were recovered as residue. No methanol was added to replace that lost by esterification. The table shows how much D.A. was separated as solids after each of the three steps.

The above results show that toluene is a very efficient extracting solvent for the dimethyl esters.

EXAMPLE 7

In this experiment several different solvents were tested against toluene and cyclohexane. The aqueous solution of Example 1 was diluted to a 20 percent solution having the solids analysis given in Example 1. Then 50 ml. CH3OH and 60 ml. of a given solvent are added to 100 ml. aqueous phase 20 percent solids (122.0 grams).

1. The above mixture is boiled 10 minutes.
2. Aqueous D.A. solution (Raffinate) and solvent layers are separated.
3. Aqueous D.A. solution is set aside for further extraction.
4. Solvent-ester solution is washed twice using 20 ml. of deionized water each time and the washing discarded.
5. Solvent is evaporated and ester recovered.
6. Aqueous D.A. solution remaining (Raffinate) is boiled for 10 minutes with another 60 ml. of solvent and extracted with solvent.
7. Repeat steps 3 and 6.

Results:

| | ESTERS EXTRACTED | | | | | | | | |
|---|---|---|---|---|---|---|---|---|---|
| Ex- | 1,1,1-Tri-chlorethane | | Benzene | | Toluene | | Isopropyl ether | | Cyclo-hexane | |
| tract | Gms. | % | Gms. | % | Gms. | % | Gms. | % | Gms. | % |
| 1st | 9.5 | 38.9 | 9.35 | 38.3 | 9.1 | 37.3 | 4.35 | 17.8 | 0.7 | 2.9 |
| 2nd | 5.65 | 23.1 | 5.30 | 21.7 | 4.7 | 19.3 | 4.15 | 17.0 | 0.7 | 2.9 |
| 3rd | 2.55 | 10.5 | 2.35 | 9.6 | 2.4 | 9.8 | 1.9 | 7.8 | 0.4 | 1.6 |
|  | 17.70 | 72.5 | 17.00 | 69.6 | 16.2 | 66.4 | 10.4 | 42.6 | 1.8 | 7.4. |

This table shows that 1,1,1-trichlorethane, benzene, and toluene, etc. are very good solvents for extraction, whereas cyclohexane is not as efficient.

EXAMPLE 8

In another example, 35 grams of a 70 percent solution having the same solids analysis as Example 1 and containing the same weight of D.A. (24.4 grams) was boiled with 50 ml. CH3OH and 60 ml. solvent. The treatment was the same as in Example 7 and the results are recorded below.

| | ESTER RECOVERED | | | | | | | |
|---|---|---|---|---|---|---|---|---|
| | Trichlor-ethylene | | 1,1,1-Tri-chlorethane | | Ethylene Dichloride | | Hexane | |
| Extract | Gms. | % | Gms. | % | Gms. | % | Gms. | % |
| 1st | 20.7 | 84.8 | 17.05 | 69.9 | 20.3 | 83.2 | 1.45 | 5.9 |
| 2nd | 4.95 | 20.3 | 4.7 | 19.3 | 2.0 | 8.2 | 2.30 | 9.4 |
| 3rd | 0.5 | 2.0 | 0.95 | 3.8 | .0 | 0 | 0.45 | 1.8 |
| TOTAL | 26.15 | 107.1 | 22.70 | 93.0 | 22.3 | 91.4 | 4.20 | 17.2 |

It is apparent that the higher concentration of the aqueous D.A. solution coupled with better solvents has increased the yield of esters so that the weight yield is up to 100 percent and the theoretical yield is as high as 90 percent.

EXAMPLE 9

This series of experiments was performed both with the solvent present and absent during the esterification and reflux. The solution has the approximate solids analysis of Example 1. The following proportions of ingredients were obtained, using the same treatment as in Example 7, with 50 ml. CH3OH; 60 ml. of the respective solvents and 50 grams 60 percent solids solution (28 grams calculated D.A.)

Two series were run. One series (A) was run as previously by boiling the solvent 10 minutes with the aqueous solution before extraction. The other series (B) was run by boiling the methanol and D.A. solution 10 minutes before each extraction, allowing the solution to cool, and then extracting with 60 ml. of solvent. The following results were obtained:

| | ESTER | | | | | | | | | | | |
|---|---|---|---|---|---|---|---|---|---|---|---|---|
| | Trichloroethylene | | | | BENZENE | | | | 1,1,1-Trichlorethane | | | |
| | A | | B | | A | | B | | A | | B | |
| Extract | Gms. | % | Gms. | % | Gms. | % | Gms. | % | Gms. | % | Gms. | % |
| 1st | 22.35 | 79.8 | 20.3 | 72.5 | 17.3 | 61.8 | 18.15 | 64.8 | 19.8 | 70.7 | 17.0 | 60.7 |
| 2nd | 4.85 | 17.3 | 4.0 | 14.3 | 5.2 | 18.6 | 4.9 | 17.5 | 4.7 | 16.8 | 2.6 | 9.3 |
| 3rd | 1.20 | 4.3 | 1.9 | 6.8 | 0.8 | 2.8 | 1.15 | 4.1 | 0.6 | 2.1 | 0.65 | 2.3 |
| TOTAL | 28.4 | 101.4 | 26.2 | 93.6 | 23.3 | 83.2 | 24.2 | 86.4 | 25.1 | 89.6 | 20.25 | 72.3 |
| Acid Value | 17 | | 32 | | 20 | | 35 | | 19 | | 42 | |

The equilibrium existing during esterification is represented by the following equation:

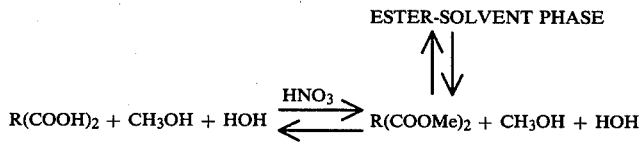

$$R(COOH)_2 + CH_3OH + HOH \underset{HNO_3}{\overset{}{\rightleftarrows}} R(COOMe)_2 + CH_3OH + HOH$$

When a solvent is used during esterification the equilibrium is shifted to the right to produce more ester.

The data above shows that boiling the solvent with the esterifying solution gives a better yield of esters than by adding the solvent after boiling. It should also be noted that the acid value of the esters recovered is low and in many cases the esters may be used as is.

EXAMPLE 10

Treatments with methylene chloride and chloroform were run, boiling the solvent with 50 grams of a 60 percent solids solution having the solids analysis given in Example 1. The procedure of Example 7 was used. The D.A. content is calculated to be 28 grams.

| | ESTER YIELD | | | |
|---|---|---|---|---|
| | Chloroform | | Methylene chloride | |
| Extract | Gms. | % | Gms. | % |
| 1st | 24.95 | 89.1 | 23.2 | 82.9 |
| 2nd | 2.45 | 8.8 | 3.4 | 12.1 |
| 3rd | 0.40 | 1.4 | 0.2 | 0.7 |
| TOTAL | 27.80 | 99.3 | 26.8 | 95.7 |

EXAMPLE 11

In this example we show how ethyl benzene compares with a 50–50 mixture of cyclohexane-benzene using a 100 grams of a 30 percent solids solution described in Example 1. The same procedure as described in Example 7 is used. The composition was composed of:
50 parts by volume CH$_3$OH
60 parts by volume cyclohexane-benzene or ethyl benzene
100 parts by weight of 30 percent solids solution (28 grams contained D.A.).

| | YIELD PARTS BY WEIGHT | | | |
|---|---|---|---|---|
| | Cyclohexane-Benzene | | Ethyl Benzene | |
| EXTRACT | Gms. | % | Gms. | % |
| 1st | 12.10 | 43.2 | 15.5 | 55.4 |
| 2nd | 7.90 | 28.2 | 6.5 | 23.2 |
| 3rd | 1.95 | 6.9 | 1.6 | 5.7 |
| TOTAL | 21.95 | 78.3 | 23.6 | 84.3 |
| Acid Value | 32 | | 20.4 | |

EXAMPLE 12

In these examples we show what effect esterification with different alcohols has on extraction with different solvents. One hundred grams of the 28 percent D.A. solution of Example 6 was used in each case.

| Column No. | 1 | | 2 | | 3 | |
|---|---|---|---|---|---|---|
| Alcohol | IPA* | | IPA | | CH$_3$OH | |
| Solvent | Cyclohexane | | 1-Cyclohexane 2-Benzene | | Benzene | |
| Solids (gms) | 30 | | 30 | | 15 | |
| | Gms. | % | Gms. | % | Gms. | % |
| 1st Extract | 0.95 | 3.4 | 3.35 | 12.0 | 11.15 | 39.8 |
| 2nd Extract | 0.80 | 2.9 | 10.40 | 37.1 | 4.4 | 15.7 |
| 3rd Extract | 0.65 | 2.3 | — | — | 1.85 | 6.6 |
| TOTAL | 2.40 | 8.6 | 13.75 | 49.1 | 17.40 | 62.1 |
| Total Reflux time | 30 Min. | | 1 hr. Solvent 1 | | 30 Min. | |
| Acid Value | 168 | | Solvent 1: 120 Solvent 2: 309 | | 24 | |

| Column No. | 4 | | 4a | | 5 | | 5a | |
|---|---|---|---|---|---|---|---|---|
| | C$_2$H$_5$OH | | | | N—C$_3$H$_7$OH | | | |
| | Benzene | | Cyclohexane | | Benzene | | Cyclohexane | |
| Solids (gms) | 15 | | 15 | | 15 | | 15 | |
| | Gms. | % | Gms. | % | Gms. | % | Gms. | % |
| 1st Extract | 11.9 | 42.5 | 4.5 | 16.0 | 20.15 | 71.9 | 16.7 | 59.6 |
| 2nd Extract | 5.9 | 21.0 | 4.25 | 15.2 | 0.9 | 3.2 | 2.15 | 7.7 |
| 3rd Extract | 1.25 | 4.5 | 1.5 | 5.7 | 0.25 | 0.9 | 0.05 | 0.2 |
| TOTAL | 19.05 | 68.0 | 10.35 | 37.0 | 21.30 | 76.0 | 18.90 | 67.5 |
| Total Reflux Time | 30 Min. | | 30 Min. | | 30 Min. | | 30 Min. | |
| Acid Value | 104 | | 16 | | 176 | | 132 | |

*Isopropyl alcohol.

The procedure used is the same as given in Example 7.

It is seen from the table above that the yield and half-ester, half-acid content vary depending on the alcohol and solvent used.

In Columns 1 and 2 we show how cyclohexane extracts an amount of the half-ester with some di-ester of ispropyl alcohol. The benzene seems to extract half-esters and some free dicarboxylic acid as well. The half-ester helps dissolve some glutaric acid.

Column 3 shows that a remarkably high yield of ester is obtainable from a dilute solution of the D.A. The ester thus produced contains little or no half-ester, half-acids and free D.A.

Column 4 shows what happens as we go up the chain length by only one carbon on the alcohol portion. Evidently, as soon as the half-ester is formed

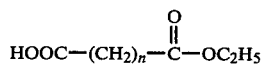

it dissolves in the benzene phase and is removed from the aqueous reaction zone so that little diester forms. Column 4a shows that cyclohexane extracts almost pure diethyl esters.

Column 5 shows that when n-propyl alcohol is used, a very good grade of half-ester is formed and extracted with benzene.

Column 5a shows cyclohexane and benzene are of the same order of selectivity when the alcohol is n-propyl.

EXAMPLE 13

This example illustrates the use of butanol and higher alcohols in making the esters and cyclohexane and benzene are used as the solvents. The same procedure was used as in Example 7 except that only one extraction was used. The solution used was 100 grams of a 15 percent solids solution having the approximate D.A. solids analysis of Example 1.

In this example, we show that when we use an alcohol which is insoluble in water, a solvent may or may not be used with butanol. A solvent is not necessary with higher alcohols. The yield may be improved by use of a solvent although it is not necessary and it may be more economical to avoid use of the solvent.

| Solvent | None | Cyclo-hexane | Benzene | None | None | None |
|---|---|---|---|---|---|---|
| Alcohol | Butanol | Butanol | Butanol | Hexanol | Octanol | Decanol |
| 1st Extract | 12.6 | 10.8 | 15.15 | 22 | 30 | 32 |
| Acid Value | 109 | 160 | 181 | 167 | 104.5 | 96 |

EXAMPLE 14

In this example we show that fluorinated and brominated solvents can be used. In all cases the following proportions of different components were used:
50 ml. CH$_3$OH
60 ml. Solvent
100 grams of 15 percent solids solution of Example 1 analysis.

The procedure of Example 7 was used, except that the 2nd extract was not refluxed. Thirty minutes contact at reflux was maintained.

| Solvent | YIELD OF ESTERS (Gms.) | | | |
|---|---|---|---|---|
| | CCl$_3$F | CCl$_2$F—CClF$_2$ | CCl$_2$FCCl$_2$F | CH$_2$Br$_2$ |
| Solvent boiling point °F. | 74.8 | 117 | 199 | 108 |
| 1st Extract | 5.55 | 4.25 | 5.6 | 6.0 |
| 2nd Extract | 3.10 | 2.35 | 3.0 | 3.2 |

EXAMPLE 15

In this example we wish to determine the influence of the amount of benzene and CH$_3$OH on the yield of esters. One hundred grams of a 15 percent solution was used having the following analysis:

| | |
|---|---|
| Succinic | 3.5% |
| Glutaric | 8.3% |
| Adipic | 2.3% |
| Other organic compounds | 1.0% |
| HNO$_3$ | 5.2% |
| Water and catalyst | 79.7% |
| | 100.0% |

| | YIELD OF ESTER WITH DIFFERENT AMOUNTS OF SOLVENT AND ALCOHOL | | | | | |
|---|---|---|---|---|---|---|
| Ester (grams) | 4.8 | 9.7 | 8.15 | 10.85 | 9.7 | 12.4 |
| Benzene (ml) | 20 | 40 | 50 | 50 | 40 | 60 |
| Methanol | 50 | 50 | 20 | 35 | 50 | 50 |
| Acid Value | 16.0 | 17.0 | 37 | 22 | 17 | 24. |

The best yield is produced using more benzene and methanol but the most economical yield on a continuous basis would most probably be at a ratio of 50/35 of benzene-methanol.

EXAMPLE 16

In order to approximate the condition existing inside a continuous esterification and extraction unit, an apparatus was set up to simulate an extractor with five stages. Five separatory funnels were filled with 100 grams each of a solution having the following analysis:

| | |
|---|---|
| Succinic acid | 5% |
| Glutaric acid | 20% |
| Adipic acid | 5% |
| Valeric acid | 5% |
| HNO$_3$* acid | 10% |
| Water | 55% |
| | 100% |

*HNO$_3$ - 70%.

To each of these funnels was added 50 ml. of methanol.

These funnels were labeled consecutively 5, 4, 3, 2, 1 and mounted vertically. Each separatory funnel was extracted with 20 ml. of benzene starting with funnel No. 1 by heating to reflux for 5 minutes with benzene solution No. 1. After the step of heating and mixing, the phases were allowed to separate and the benzene phase was moved to funnel No. 2 while solution No. 1 is removed and discarded. The heating and separation process is repeated with funnel No. 2 and the benzene is moved to No. 3 and so on through funnel No. 5. Thus the first 20 ml. of benzene passing through five stages of aqueous dicarboxylic acid-methanol solution has come to equilibrium with the highest concentration and the aqueous solutions have been depleted somewhat of their esters.

While benzene solution No. 1 moves up to solution No. 2, benzene solution No. 2 moves into funnel No. 1 which has received the solution from funnel No. 2.

Fresh aqueous D.A. solution containing methanol is added to funnel No. 5 as the aqueous solutions move down stepwise, while fresh benzene is added to funnel No. 1 as the benzene solutions move upward stepwise.

As the aqueous solutions move downward, they become more depleted in dicarboxylic acids and esters, while the benzene solutions become more concentrated as they move upward.

An equilibrium is reached after about three stages, so that no more ester can be extracted by this amount of benzene under the conditions given. In order to increase the yield per stage or per pass through the five-stage unit, it would be necessary to increase the amount of solvent or increase the amount of methanol. These concepts were discussed and shown in Examples 12 and 15.

The reaction can take place at room temperature if enough time is given the reaction. The short table below shows the yield obtained when the reaction is allowed to take place at room temperature using 100 grams of 35 percent D.A. solution given above, 60 ml. benzene, and 50 ml. of $CH_3OH$.

| TIME 25° C. | YIELD |
| --- | --- |
| 5 min. | 2.45 grams |
| 60 min. | 8.2 " |
| 16 hours | 22.0 ". |

Our tests have also shown that the five minute reaction time gave mainly dimethyl succinate. Benzene was used as the solvent and methanol as the alcohol. Benzene extract from one funnel was transferred to the next funnel through the entire series and the aqueous solution of the reaction mixtures was transferred from one funnel to the next funnel through the entire series in the reverse direction, to simulate countercurrent extraction. It was found that equilibrium was reached after about three stages, so that no more ester was extracted by this amount of benzene under the conditions given, so that three extractions of methyl esters in the foregoing examples, roughly approximates the results obtained with countercurrent extraction. In order to increase the yield per stage or per pass through the five-stage experimental unit, it would be necessary to increase the amount of solvent or increase the amount of methanol.

The contents of the various separatory funnels were heated to approximately the refluxing temperature. In each of the previous examples, the esters were formed by heating to the refluxing temperature. Temperatures in excess of the refluxing temperature may be obtained by placing the material being esterified under pressure. Such increases in temperature, even to 150° or 200° C. may be used, but heating is not essential as esterification takes place at room temperature, although slowly.

EXAMPLE 17

In this example, we show the use of cyclohexanone. The use of cyclohexanone is more critical to the aqueous solids concentration than most of the solvents referred to in the other examples.

If the 35 percent aqueous solution of Example 16 is used with the procedure of Example 7, we find that we obtain the following yields when a 50—50 mixture of cyclohexanone and cyclohexane is used and when cyclohexanone is used.

| | ESTER YIELD, GRAMS | |
| --- | --- | --- |
| | 50-50 Mixture | Cyclohexanone |
| 1st Extract | 2.0 | No separation |
| 2nd Extract | 3.2 | No separation |

When a 25 percent aqueous solution is used of the same solids analysis we obtain the following:

| | | |
| --- | --- | --- |
| 1st Extract | 3.0 | 1.2 |
| 2nd Extract | 3.6 | 1.1 |

When a 15 percent aqueous solution is used we obtain:

| | | |
| --- | --- | --- |
| 1st Extract | 3.9 | 2.0 |
| 2nd Extract | 3.4 | 2.1 |

Thus, cyclohexanone can be used as such or in combination with other solvent but care must be taken with the concentrations of the aqueous phase. It was also learned that the amount of methanol has an important effect because the methanol can act as a coupler and thus prevent the formation of distinct phases. Other higher molecular weight ketones such as dipropyl ketone are not as sensitive to concentrations.

I claim:

1. In a continuous process for the treatment of the mother liquor which results from the nitric acid oxidation of cyclohexanol and/or cyclohexanone and the recovery of the valuable components therefrom, which mother liquor contains a mixture of aliphatic dibasic acids, nitric acid and metal catalysts values, the improved process comprising:
   (a) continuously contacting said mother liquor with an organic alcohol of the formula ROH wherein R is alkyl of 4 to about 20 carbon atoms and which alcohol will form esters which are not miscible with the resulting aqueous phase, and in a sufficient amount to esterify at least a portion of the dibasic acids;
   (b) allowing the organic esters to form a separate organic phase from an aqueous phase;
   (c) separating said organic phase and said aqueous phase; and
   (d) recycling said aqueous phase containing nitric acid and metallic catalyst components to the nitric acid oxidation reaction.

2. The process of claim 1 which includes the step of recovering the esters from the organic phase.

3. The process of claim 1 which includes the step of recovering alcohol after separating the aqueous phase from the organic phase and recycling the alcohol to the esterification step.

4. The cyclic process of producing esters of the class consisting of esters of the organic acids adipic, glutaric and succinic and mixtures thereof, which comprise oxidizing source material which contains six carbon atoms in a saturated straight or cyclic chain and is oxidizable by nitric acid to organic acids, using nitric acid and soluable oxidation catalysts in an aqueous solution, thereby producing at least some of the aforesaid organic acids, esterifying the aforesaid organic acids in aqueous solution with water-immiscible alcohol, forming an aqueous phase and an organic phase separating the resulting aqueous phase which includes nitric acid and catalysts from the organic phase, which includes esters of the aforesaid organic acids, and reusing the aqueous solution which contains water soluable catalyst and nitric acid in oxidation of further source material.

5. The process of claim 4 in which the source material is cyclohexanone.

6. The process of claim 4 in which the source material is cyclohexanol.

7. The process of claim 4 in which the source material is cyclohexane.

8. The process of claim 4 in which the source material is a mixture of cyclohexanone and cyclohexanol.

9. The process of claim 4 which includes the step of recovering alcohol after separating the aqueous phase from the organic phase and recycling the alcohol to the esterification step.

* * * * *